US006548025B1

(12) United States Patent
Rasouli et al.

(10) Patent No.: US 6,548,025 B1
(45) Date of Patent: Apr. 15, 2003

(54) APPARATUS FOR GENERATING ODOR UPON ELECTRONIC SIGNAL DEMAND

(75) Inventors: Firooz Rasouli, Midlothian, VA (US); Hamid Arastoopour, Downers Grove, IL (US); Ali Oskouie, Chicago, IL (US)

(73) Assignee: Illinois Institute of Technology, Chicago, IL (US)

( * ) Notice: Subject to any disclaimer, the term of this patent is extended or adjusted under 35 U.S.C. 154(b) by 43 days.

(21) Appl. No.: 09/708,699

(22) Filed: Nov. 8, 2000

(51) Int. Cl.[7] .................................................. A61L 9/00
(52) U.S. Cl. ........................ 422/123; 422/4; 422/108; 422/124; 422/125; 422/305; 422/306
(58) Field of Search ................................ 422/123, 124, 422/125, 305, 108, 306, 4; 239/57, 60; 428/64.2

(56) References Cited

U.S. PATENT DOCUMENTS

| | | |
|---|---|---|
| 2,562,959 A | 8/1951 | Stern |
| 2,871,526 A | 2/1959 | Bulloff |
| 4,009,384 A | 2/1977 | Holland |
| 4,037,352 A | 7/1977 | Hennart et al. |
| 4,556,539 A | 12/1985 | Spector |
| 4,603,030 A | 7/1986 | McCarthy |
| 4,604,114 A | 8/1986 | Ward |
| 4,905,112 A | 2/1990 | Rhodes |
| 5,023,020 A | 6/1991 | Machida et al. |
| 5,069,876 A | 12/1991 | Oshinsky |
| 5,069,877 A | 12/1991 | Pozzo |
| 5,178,839 A | 1/1993 | Spector |
| 5,217,696 A | 6/1993 | Wolverton et al. |
| 5,273,690 A | 12/1993 | McDowell |
| 5,424,049 A | 6/1995 | Giolitti et al. |
| 5,565,148 A | 10/1996 | Pendergrass, Jr. |
| 5,574,821 A | 11/1996 | Babasade |
| 5,591,409 A | 1/1997 | Watkins |
| 5,734,590 A | 3/1998 | Tebbe |
| 6,004,516 A | * 12/1999 | Rasouli et al. ............... 422/124 |
| 6,214,433 B1 | * 4/2001 | Tronche et al. ............ 428/64.1 |
| 6,241,944 B1 | * 6/2001 | Budman ........................ 422/4 |
| 6,328,287 B2 | * 12/2001 | Wittek .......................... 261/30 |

FOREIGN PATENT DOCUMENTS

| | | |
|---|---|---|
| EP | 0 123 746 | 11/1984 |
| EP | 0 238 983 | 9/1987 |
| FR | 2 501 468 | 9/1982 |
| GB | 2 279 010 | 12/1994 |
| WO | WO 99/08174 | * 2/1999 |

OTHER PUBLICATIONS

Hiroo Iwata et al.: *Preparation of temperature–sensitive membranies by graft polymerization onto a porous membrane*, Journal of Membrane Science, 55, pp. 119–131, 1991.

* cited by examiner

*Primary Examiner*—Robert J. Warden, Sr.
*Assistant Examiner*—Sean E. Conley
(74) *Attorney, Agent, or Firm*—Pauley Petersen Kinne & Erickson

(57) ABSTRACT

An apparatus for generating odor including a disk having a substrate with a dispersing material retaining at least one releasable aroma positioned with respect to the substrate. The dispersing material includes a structure, such as a plurality of openable pores, that is physically responsive to a stimulus such as heat or light. A device provides the stimulus to the dispersing material upon demand as a function of a signal, wherein the plurality of pores within the dispersing material are reversibly enlarged as a result of the stimulus.

39 Claims, 4 Drawing Sheets

APPARATUS FOR GENERATING ODOR UPON ELECTRONIC SIGNAL DEMAND

BACKGROUND OF THE INVENTION

1. Field of the Invention

This invention relates to an apparatus for generating odor in which a signal, possibly from a remote location, activates an aroma.

2. Description of the Prior Art

The Internet is a relatively new and quickly developing medium for information transfer and all forms of commerce. Internet access allows the user, through an ordinary telephone line, to view true multimedia clips, including text, pictures, audio and video. One current void on the Internet is the ability for a consumer to sample scents and aromas of food products, perfumes, flowers, wines and other products wherein the scent of the product is an important factor.

The prior art teaches several methods of distributing a specific scent on demand. The application of heat is a known method of diffusing perfumes or other odorants into the atmosphere. Pozzo, U.S. Pat. No. 5,069,877 teaches a method and apparatus wherein heat is applied, from a source such as a lightbulb, to a perfume-impregnated heat shrink material, thus diffusing the perfume into the air. Holland, U.S. Pat. No. 4,009,384, teaches a similar apparatus wherein heat, from a lightbulb, is applied to a porous, perfume-impregnated, temperature-resistant material.

Stern, U.S. Pat. No. 2,562,959 teaches a system wherein compressors pump various scents through air pipes depending on an electromechanical signal generated by a film. The various scents are stored in liquid form until selected for dispersal when they are vaporized and distributed through compressed air pipe lines.

There is a need, however, for an apparatus that permits a user to access any number of specific scents or fragrances, specifically through a signal provided from a remote location such as an Internet server.

SUMMARY OF THE INVENTION

It is one object of this invention to provide an apparatus which enables the user to sample various scents from a single disk.

It is another object of this invention to provide an apparatus that interfaces with a remote location and distribute selected scents based upon a predetermined signal.

It is still another object of this invention to provide an apparatus that interfaces with a personal computer to provide various scents based upon a predetermined signal.

It is yet another object of this invention to provide an apparatus that emits a selectable scent when an electric current is applied to the apparatus.

A user of the subject apparatus preferably operates a computer having a disk drive according to this invention, called a Tele-Aroma Drive (TAD). In one preferred embodiment of the subject invention, a user connects to a web site that is compatible with the subject apparatus and selects a specific scent from a computer menu. A controller, preferably contained within the disk drive generates an appropriate thermal or electrical signal to an exhaust and/or a disk containing an adsorbent. The adsorbent then disseminates the proper concentration of a scent into the user's environment.

The disk, preferably comprising a substrate and the adsorbent, is used as the means for delivery of the various scents or fragrances. In one preferred embodiment of this invention, a plurality of alternating strips of conductive material and non-conductive material are arranged on the substrate of a disk having a rectangular shape. In another preferred embodiment of the subject invention, a plurality of alternating concentric strips of conductive material and non-conductive material are arranged on the substrate of a circular disk. The adsorbent, such as a semi-porous polymer membrane, is preferably applied to the conductive material on the substrate.

A controller generates a signal, either thermal or electrical, to the disk and/or an exhaust. The controller preferably regulates the flow of electricity among power source, the disk and the exhaust. The controller preferably gathers signals from a user or a remote location such as a server, based upon predetermined characteristics of specific scent/adsorbent combinations.

A heater, such as a laser or a conductive element, heats the adsorbent depending on the specific signal received from the controller. The adsorbent, while heated, emits the specific scent from the disk. The exhaust passes a fluid, preferably air, over the adsorbent on the disk to distribute the scent emitted from the adsorbent into the environment.

The entire apparatus according to this invention is preferably housed within a disk drive, similar to a floppy disk drive used with personal computers. The disk drive can be connected to a computer with a dedicated card or through a printer port. In another preferred embodiment, a disk drive, similar to a CD-ROM drive used with personal computers, accommodates the disk formed from an arrangement of alternating concentric rings of conductive material and non-conductive material. In this preferred embodiment of this invention, the laser is used to heat up the adsorbent and/or the adsorbate.

According to another preferred embodiment of this invention, an apparatus for generating odor requires a disk including a substrate and a dispersing material retaining at least one releasable aroma positioned on the substrate. A device is connected with respect to the disk to provide a stimulus to the dispersing material upon demand as a function of a signal. As a result of the stimulus, at least one physical property of the dispersing material is altered.

The dispersing material may comprise a smart material structure having reversible properties, such as PNIPAAM, allyl-substituted polyethylene glycol cross-linked by a silicon-based compound, allyl-substituted polyethylene glycol cross-linked by tetrakis (dimethylsiloxy) silane, a silicone formulation and/or combinations thereof, having a plurality of openable pores or an otherwise alterable physical structure; stimuli-response membranes that burst in response to the stimulus; an immiscible combination of polymer solution and aroma compound; or a polymer material insensitive to a wavelength of emitted light.

According to alternative embodiments of this invention, the device may be a laser providing a thermal or optical stimulus or may be some other device providing a chemical stimulus, an optical stimulus, a thermal stimulus, a magnetic stimulus and/or an electromagnetic stimulus.

According to one preferred embodiment of this invention, the disk for generating odor includes the substrate having a first side and a second side. A first readable medium containing text, picture, audio and/or video is positioned on the first side of the substrate. A second readable medium containing a releasable odor is then positioned on the second side of the substrate opposite the first side. Such a disk may then be used in connection with a specialized piece of equipment capable of reading two side of the disk simultaneously and emitting any combination of text, picture, audio, video and/or aroma.

BRIEF DESCRIPTION OF THE DRAWINGS

The above-mentioned and other features and objects of this invention will be better understood from the following detailed description taken in conjunction with the drawings wherein.

DESCRIPTION OF THE PREFERRED EMBODIMENTS

Figure 1:
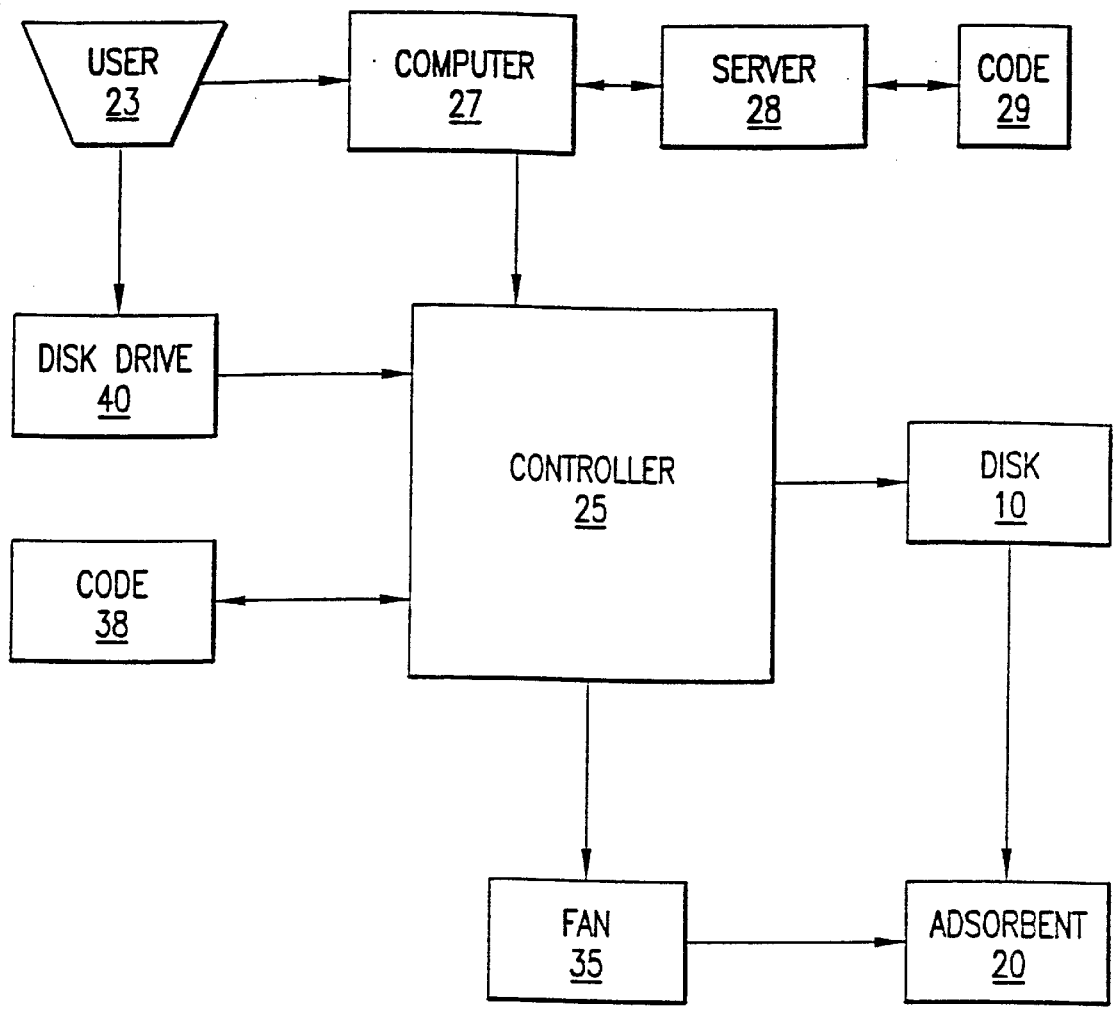
FIG. 1 is a flowchart of the interaction among the various components of the subject invention according to one preferred embodiment of this invention.

FIG. 1 shows a flowchart of the interaction among the various components of the apparatus according to one preferred embodiment of this invention. As shown in FIG. 1, user 23 of the subject apparatus preferably operates computer 27 with disk drive 40, also called a Tele-Aroma Drive or TAD.

In one preferred embodiment of the subject invention, user 23 connects from computer 27 to a web site on server 28 that is compatible with the subject apparatus. User 23 selects a specific scent from a menu, such as a perfume. Server 28 receives the signal from computer 27 and consults server code 29 for the proper signal to transmit back to computer 27. Server 28 transmits a return signal back to computer 27 based upon parameters of the selected perfume. This return signal is decoded by controller 25, which is preferably but not necessarily contained within disk drive 40. Controller 25 consults controller code 38 to generate the appropriate thermal or electrical power to fan 35 and/or disk 10 containing adsorbent 20. Given the proper power, adsorbent 20 disseminates the proper concentration of scent into an environment surrounding user 23.

Figure 2:
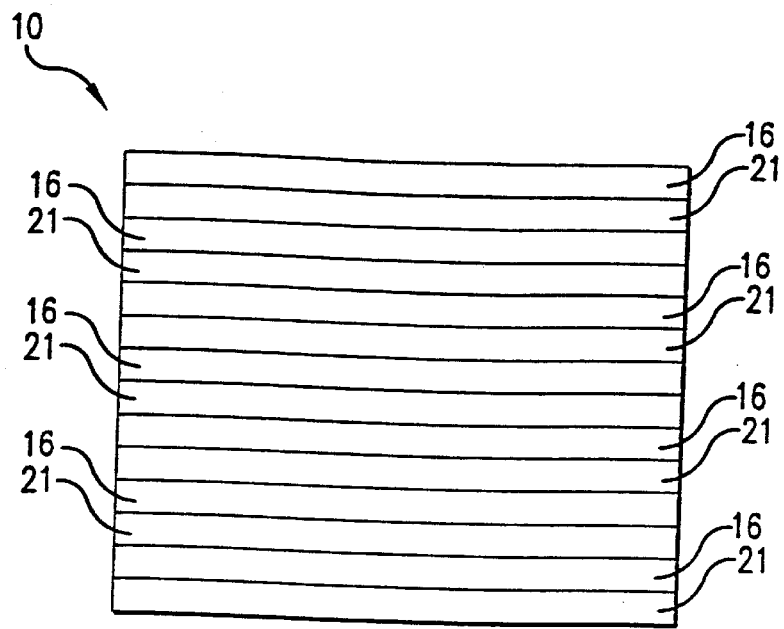
FIG. 2 is a diagrammatic top view of a disk according to one preferred embodiment of this invention.

An apparatus for generating odor utilizes disk 10 such as that shown in FIG. 2. Disk 10 preferably comprises two basic components: a substrate and adsorbent 20. Substrate, as used in this specification, is a generic term referring to the basic composition or support material of disk 10. Substrate material is preferably a polymer or other suitable non-conductive material.

Figure 4:
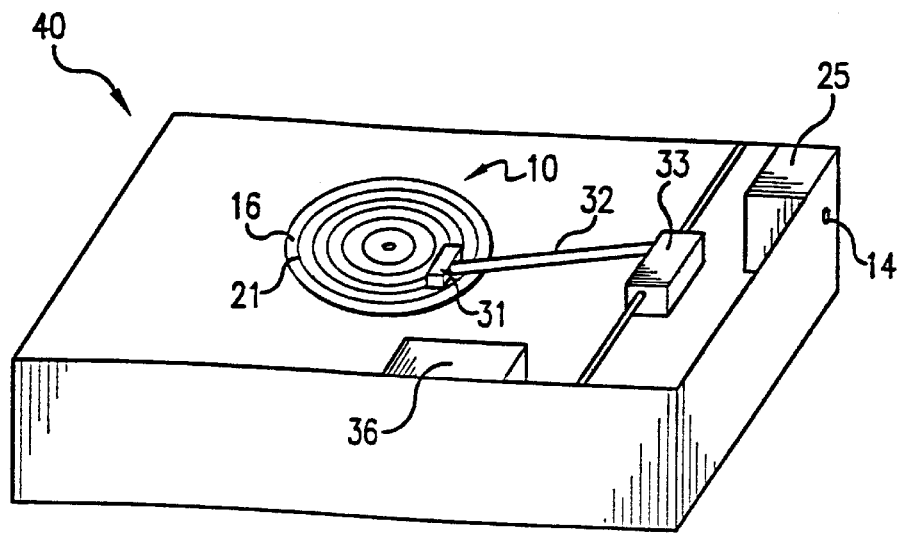
FIG. 4 is a diagrammatic perspective view of the apparatus according to another preferred embodiment of this invention.

In one preferred embodiment of this invention shown in FIG. 2, a plurality of alternating strips of conductive material 16 and non-conductive material 21 are arranged on the substrate of disk 10 having a rectangular shape. FIG. 4 shows another preferred embodiment of the subject invention in which a plurality of alternating concentric strips of conductive material 16 and non-conductive material 21 are arranged on the substrate of disk 10 having a circular shape.

Conductive material 16 may be a highly conductive metal such as aluminum or copper, or a conductive non-metal such as carbon. The strips or rings of conductive material 16 are preferably connected together with non-conductive material 21 to allow the strips of conductive material 16 to heat up or accept an electrical current independently of other strips of conductive material 16.

Adsorbent 20, as used in this specification, is a generic term referring to material that adsorbs desired odor-producing chemicals, such as aroma solutions and perfumes. The function of adsorbent 20 is to adsorb the odor-producing chemical when treated and desorb the odor-producing chemical when a stimulus, such as heat or high temperature air flow, is applied.

Adsorbent 20 is selected based upon several important criteria. Adsorbent 20 must have reasonable permeability. It is preferable that the characteristics of adsorbent 20 allow for the transport of aroma solution. Adsorbent 20 must also have a high capacity for the aroma solution. An ideal adsorbent 20 should retain a large amount of aroma solution per unit volume of adsorbent 20. Adsorbent 20 should also possess indiscriminate permeability to all ingredients of the aroma solution. An ideal adsorbent 20 will pass all components of the aroma solution evenly. Adsorbent 20 should also be inert such that no chemical interaction takes place between adsorbent 20 and the aroma solution. Adsorbent 20 should not desorb the aroma solution at temperatures under 100° F. Finally, adsorbent 20 should possess a resistance to high and variant temperatures, between 120° F. and 500° F., and cyclical heating and reheating such that adsorbent 20 characteristics do not change.

In one preferred embodiment of this invention, adsorbent 20 is applied to conductive material 16 on the substrate. Adsorbent 20 may be a gel, a paste or any other material that exhibits the characteristics described above. Other possible adsorbent 20 materials include: packing materials used in chromatography such as Chromosorb 101™, Porpak Q™, Apiezon L™, Carbowax20 M™, OV-210™, and/or Dexsil 300 GC™; inorganic materials such as silica gel, activated carbon, carbon fiber, and/or zeolites; synthetic polymers and responsive polymeric materials that exhibit changes in properties in response to a control variable such as temperature or light; and/or organic compounds such as cellulose compounds, waxes or natural pastes made with mixtures of finely sifted sawdust and syrup of gum arabic.

In a preferred embodiment of this invention, adsorbent 20 is a semi-porous membrane 22. Specifically, such materials as Teflon, Tygon, silicon rubber or other polymers may be used as adsorbent 20. Silicon rubber demonstrates favorable results according to the desired characteristics listed above for an ideal adsorbent 20. In the embodiment of this invention wherein adsorbent 20 is a polymer such as semi-porous membrane 22, adsorbent must be treated in one of several methods to suspend the aroma solution or fragrance within pores of adsorbent 20. In an alternate preferred embodiment of this invention, key chemical ingredients can be mobilized in adsorbent 20, and by selective precise heating of combinations of such key chemical ingredients, various odors can be generated in-situ.

As shown by the flow chart in FIG. 1, controller 25 generates a signal to an input of the apparatus. The signal is dependent upon specifications or characteristics entered by user 23 from personal computer 27 or by a vendor from server computer 28. Controller 25 preferably regulates the flow of electricity among power source (not shown in FIG. 1), disk 10 and exhaust 35. As discussed above, controller 25 also gathers signals from a user or a remote location such as server 28 shown in FIG. 1 and, based upon predetermined characteristics of specific aroma solutions and adsorbents 20, generates an input, either thermal, mechanical or electrical, to disk 10 and/or exhaust 35.

Figure 6:
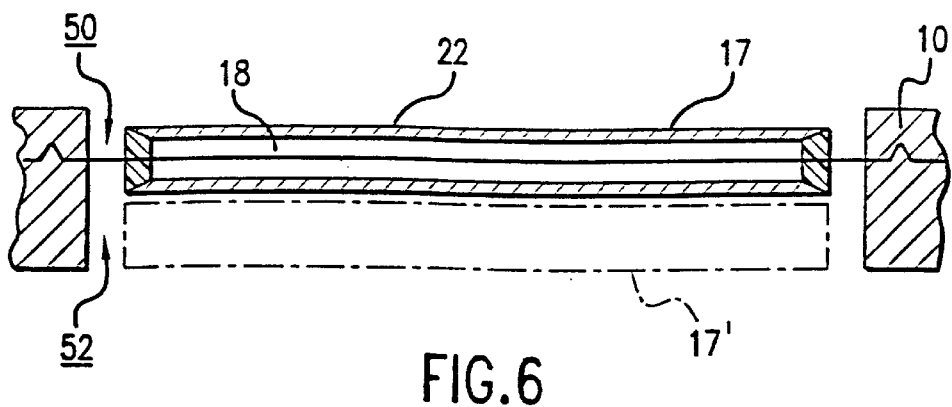
FIG. 6 is a diagrammatic cross-sectional side view of a membrane module according to one preferred embodiment of this invention.

Heater 30, such as laser 31 shown in FIG. 4 or conductive element 18 shown in FIG. 6, heats adsorbent 20 depending on the specific signal received from controller 25. Heater 30 reaches a predetermined temperature based upon a signal received from controller 25. The predetermined temperature is calculated based upon the chemical properties of the aroma solution to be distributed as well as the characteristics of the specific adsorbent 20. Each aroma solution/adsorbent 20 combination may require a slightly different temperature to effectively separate the scent from adsorbent 20. In one preferred embodiment of this invention, heater 30 is conductive element 18, such as that shown in FIG. 6 and discussed below. When a current is applied to conductive element 18, a desired temperature is attained with slight variations of the applied current.

In one preferred embodiment of this invention, a predetermined temperature is achieved by controlling the time of heating instead of the temperature of conductive element 18. Timed heating thus eliminates the need for a thermocouple connected to conductive element 18.

In another preferred embodiment of this invention, shown in FIG. 4, laser 31 is used to generate heat within adsorbent 20. If laser 31 is used as heater 30, an arrangement of alternating conductive material 16 and non-conductive material 21 is unnecessary. Like a CD-ROM disk, disk 10 in this preferred embodiment can be fabricated entirely from a non-conductive substrate, and adsorbent 20 can be arranged in concentric rings on such non-conductive substrate.

In yet another preferred embodiment of this invention, heater 30 may comprise a blower producing a high temperature, high temperature air flow. In this embodiment, high temperature gas, such as air, is discharged across the surface of adsorbent 20 to generate heat in adsorbent 20.

Adsorbent 20, while heated or exposed to a high-temperature, high-velocity gas, emits the specific aroma from disk 10. According to one preferred embodiment of this invention, exhaust 35, such as fan or blower 36, passes a fluid, preferably air, over adsorbent 20 on disk 10 and preferably through vents 45 in disk drive 40. In another preferred embodiment of this invention, exhaust 35 may discharge a high temperature air flow which initiates fast evaporation or sublimation of the aroma solution on adsorbent 20. Exhaust 35 preferably distributes the scent emitted from adsorbent 20 into the environment surrounding user 23, enhances adsorption of the scent, and cools heater 30 and adsorbent 20 to slow dissipation of further scent when a new scent is selected or the current scent is satisfactorily distributed. The combined distribution and cooling action of exhaust 35 avoids mixing multiple fragrances during extended use of the apparatus.

In another preferred embodiment of this invention, adsorbent 20 such as at least one membrane module 17 having semi-porous membrane 22, as shown in FIG. 6, is moveable from a first position to a second position within apparatus, such as disk 10. In this preferred embodiment, membrane module 17, when selected, moves from a first position in upper compartment 50 to a second position in lower compartment 52. Lower compartment 52 is preferably positioned within a discharge path of exhaust 35. This preferred embodiment of this invention prevents excess mixing of scents of the selected membrane module 17' with unselected membrane modules 17. Controller 25 preferably controls the movement of adsorbent 20 such as membrane module 17, 17' from a first position to a second position and vice versa.

The entire apparatus according to this invention is preferably housed within disk drive 40, much like a stagnant 3.5" floppy disk drive. Disk drive 40 is preferably not larger than a typical computer speaker, and may be purchased by a consumer like any other personal computer peripheral device. Disk drive 40 can be connected to computer 27 with a dedicated card or through a printer port to input 14 of disk drive 40. Disk 10 is preferably inserted into disk drive 40 which is configured with computer 27.

Figure 3:
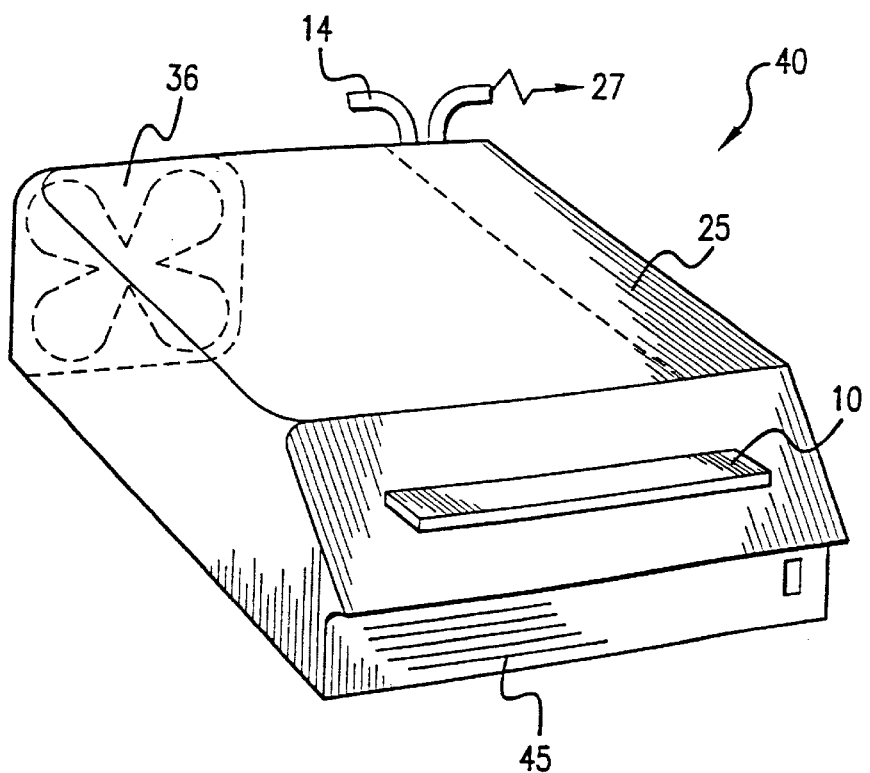
FIG. 3 is a diagrammatic perspective view of the apparatus according to one preferred embodiment of this invention.

In one preferred embodiment of this invention shown in FIG. 3, disk drive 40 accepts disk 10 such as that shown in FIG. 2. In disk drive 40 shown in FIG. 3, controller 25 applies various currents and/or thermal energy to strips of conductive material 16 or a matrix of conductive elements 18, such as those in membrane module 22 shown in FIG. 6.

Another preferred embodiment of this invention is shown in FIG. 4, wherein disk drive 40 having input 14 accommodates disk 10 formed from an arrangement of alternating concentric rings of conductive material 16 and non-conductive material 21. Disk drive 40 shown in FIG. 4 is configured similar to a CD-ROM drive used with personal computers. Disk drive 40 comprises actuator motor 33 which controls actuator arm 32 to position laser 31 at a predetermined radius of disk 10. A disk motor (not shown) rotates disk 10 so that laser 31 heats a specific concentric ring preferably layered with adsorbent 20.

Figure 7:
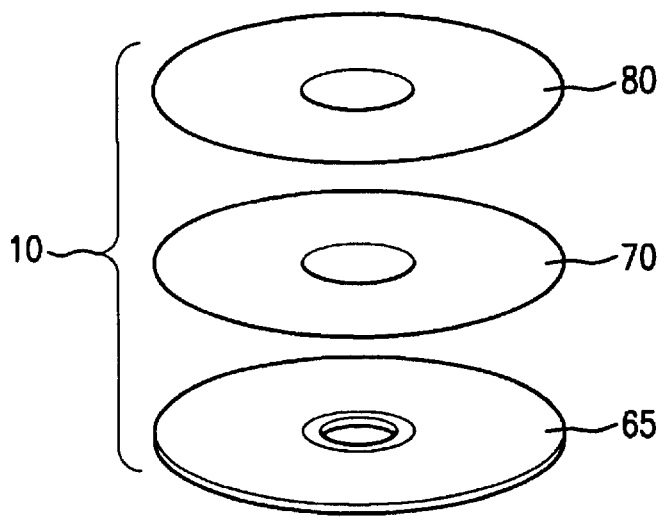
FIG. 7 is an exploded perspective view of a disk according to one preferred embodiment of this invention.
Figure 8A:
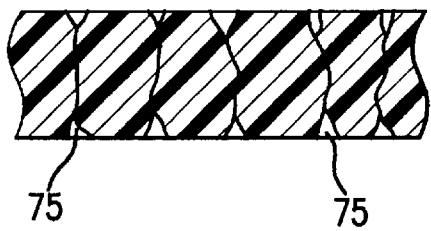
FIG. 8A is a diagrammatic cross-sectional view of dispersing material prior to application of a stimulus according to one preferred embodiment of this invention.
Figure 8B:
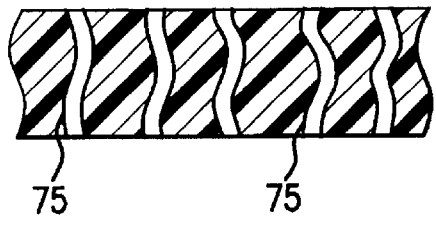
FIG. 8B is a diagrammatic cross-sectional view of dispersing material shown in FIG. 8A after application of the stimulus.

According to one preferred embodiment of this invention, and as discussed in more detail below, an apparatus for generating odor may include disk 10 wherein substrate 65 includes a dispersing material 70 retaining at least one releasable aroma, as shown in FIGS. 7 and 8. Device 60 is preferably operatively connected with respect to disk 10 and provides a stimulus to dispersing material 70 upon demand as a function of a signal, wherein at least one physical property of dispersing material 70 is altered as a result of the stimulus. In a preferred embodiment of this invention, dispersing material 70 includes a microscopic structure of a plurality of openable pores 75 such as shown in FIGS. 8A and 8B. FIG. 8A shows a magnified cross-sectional view of openable pores 75 in dispersing material 70 prior to application of a stimulus. Subsequent to the application of a stimulus, such as heat or light, openable pores 75 expand and permit an aroma trapped within or beneath dispersing material 70 to be released, as shown in FIG. 8B.

Device 60 according to various preferred embodiments of this invention may provide a chemical stimulus, an optical stimulus, a thermal stimulus, a magnetic stimulus, an electromagnetic stimulus or any other stimulus known to those having ordinary skill in the art. One illustrative device 60 as described above and hereinafter is laser 31 which may provide a thermal stimulus and/or an optical stimulus to dispersing material 70.

According to another preferred embodiment of this invention, dispersing material 70 containing a releasable aroma, providing a similar result but in a different manner from adsorbent 20, is positioned on substrate 65 of disk 10. Dispersing material 70 can be fabricated from a polymer, gel, smart material or a smart material grafted or bonded on another porous polymer such as polyvinyliddene fluoride, silicone compounds, polysolofone, cullulose fibers or polystyrene. Dispersing material 70 may also be a conductive polymer. Suitable smart materials preferably include permoselective, temperature or light sensitive polymeric membranes or gels having a plurality of openable pores 75. Thermal, optical and/or chemical stimuli are exerted on or within the smart material and reversibly enlarge and contract the pores 75, resulting in controlled release of aroma, vapors and/or liquids. Such dispersing materials 70 can be chemically grafted or physically adsorbed onto solid polymer supports and permit a rapid change of surface film thickness or pore size upon changing the surface temperature. The responses can be much faster for solids as hydrogels since the surface coating can be very thin.

Figure 9A:
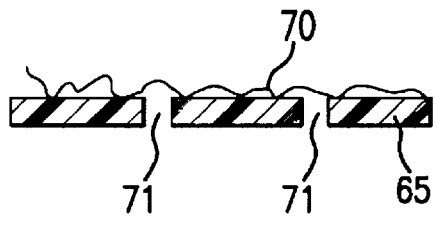
FIG. 9A is a diagrammatic cross-sectional view of dispersing material prior to application of a stimulus according to one preferred embodiment of this invention.
Figure 9B:
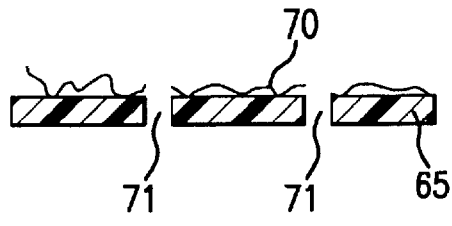
FIG. 9B is a diagrammatic cross-sectional view of dispersing material shown in FIG. 9A after application of the stimulus.

As indicated, dispersing material 70 may comprise a smart material grafted or bonded to a porous polymer substrate 65 as shown in FIGS. 9A and 9B. FIG. 9A shows a magnified cross-sectional view of such a structure prior to application of a stimulus. Subsequent to the application of the stimulus, smart material 70 shrinks, resulting in the opening of fixed pores 71 positioned in substrate 65, as shown in FIG. 9B. According to one preferred embodiment of this invention, substrate 65 may comprise a porous metal or alloy having a high thermal expansion coefficient coated with a thin layer of dispersing material 70, for example a polymer. In practice, the porous metal or alloy will expand in response to a stimulus, such as heat or electrical energy, causing the polymer to stretch and become thinner. As a result, the aroma diffuses from fixed pores 71 of the porous metal. When the porous metal cools down and contracts, so the stretched polymer elastically returns to its initial thickness, hindering the diffusion of the aroma from the polymer.

The behavior of the above mentioned dispersing material 70 is due to the phase separation above a lower critical solution temperature (LCST), which corresponds to the minimum in the lower precipitation temperature (LPT). For example, Poly N-isopropylacrylamide (PNIPAAM) when grafted on polyvinylidene floride (poly VdF) in aqueous solution results in an LCST of around 31–33° C. The hydrated PNIPAAM chain shrinks significantly when the temperature is raised to its LPT. On the other hand, above the LPT, grafted polymer chains shrink and precipitate on the membrane, resulting in the opening of pores 75. The result is an increase of the permeation rate. Similar results may be obtained with alternative dispersing materials 70 such as allyl-substituted polyethylene glycol cross-linked by a silicon-based compound, allyl-substituted polyethylene glycol cross-linked by tetrakis (dimethylsiloxy) silane, a silicone formulation or combinations thereof. Opposite results may occur for diffusional permeation and a reduction of permeation at higher temperatures. The difference might be due to the grafting amount. The critical temperature can be tailored by copolymerizing with other monomers.

Another alternative embodiment of this invention involves dispersing material 70 comprising a polymer material that is not sensitive to the wavelength of laser 31. When laser 31' shines on the polymer material, it can pass through the polymer material without burning the polymer material. Therefore, all of the laser power is used to increase the vapor pressure of odorous fluid causing such fluid to permeate from the polymer layer. Other alternatives include N-isopropylacrylamide grafted to cellulose fibers or polystyrene to create thermoreversible adsorbents. In addition, polytacrylic acid, pluronic polyols, viscoelastic smart gels and/or microencapsulation polymers may also be used.

An alternative method and apparatus according to this invention involves the use of dispersing material 70 comprising stimuli-response membranes as microcapsules to entrap the odor making chemicals in the inner surfaces. These kind of materials are currently being used in various applications from sludge de-watering applications and printing to biological drug delivery and food technology. One encapsulation method is used to make novelty "scratch and sniff" materials. Tiny encapsulated spheres with different odorous materials can be glued to various concentric substrates. The spheres burst and release odor when exposed to laser heat or electrically heated elements.

One other preferred embodiment of dispersing material 70 is encapsulation of an aroma source using a coacervation process, similar to that used in the food industry. An aroma compound is dispersed by agitation in a polymer solution. For the method to work, the aroma compound and the polymer solution should be immiscible. As an example, for non-aqueous aroma compounds, the aroma can be dispersed in an aqueous gelatin solution. For aqueous aroma solution, a polymer such as ethylcelluoulose soluble in a non-polar solvent such as cyclohexane may be selected. A second water soluble polymer, such as gum Arabic, may be then added to this emulsion. The coacervation or phase separation phenomenon is then achieved by changing the temperature and/or acidity of the resulting polymer solution. After mixing the above polymer solution, dilute acetic acid is added to adjust the acidity of the solution. As a result, two immiscible liquid phases are created with different amounts of solubilized polymer in each phase. The supernatant phase has low polymer concentrations, whereas the coacertive phase has a relatively high concentration of the polymers.

Dispersing material 70 can also be of electrically conductive or magnetic in nature. Dispersing material 70 can be configured in various shapes including hollow fiber, sold fiber, circular strip, rectangular strip, etc.

As discussed above, laser 31 may be used as a source of stimulation. The stimulation from laser may be in the form of heat energy or because of the optical characteristics of the laser source. The target sites on disk 10 can become active in response to change in temperature or the wavelength of laser 31. Such stimulations can cause changes in the sizes of pores 75 of dispersing material 70, shrinkage of the porous microstructures, alignment of the molecules at the target site or enhanced diffusion of the encapsulated aromatic compounds through semi-permeable barriers.

According to a preferred embodiment of this invention, laser 31 may comprise a diode laser, using semi-conducting materials similar to those used in electrical diodes and transistors. Such lasers are inexpensive and compact. Diode lasers have wavelengths throughout much of the visible spectrum, but the most common diode lasers emit light in the near infrared region (780 nm). Similar to CD-ROMs, the storage capacity of disks 10 can be increased by using diode lasers with wavelengths as short as possible. Other possibilities include dye lasers and chemical lasers.

According to an alternative preferred embodiment of this invention, for the electrically conductive or magnetic adsorbents, the stimuli can be produced by an electrical source, magnet or an electromagnetic source.

Reflective layer 80 may be positioned on dispersing material 70 to complete disk 10. The reflective layer 80 can be gold, silver, aluminum or other suitable material to reflect the laser beam back to dispersing material 70.

Figure 10:
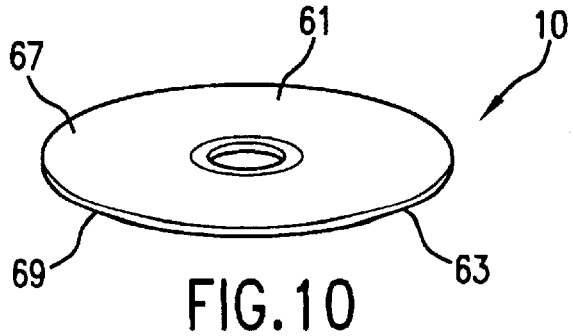
FIG. 10 is a perspective view of a disk according to one preferred embodiment of this invention.

Disk 10, according to a preferred embodiment of this invention shown in FIG. 10, may comprise substrate 65 having a first readable medium 67 containing at least one of audio and video positioned on a first side 61 of substrate 65. A second readable medium 69 containing a releasable odor is positioned on a second side 63 of the substrate. Second readable medium 69 may comprise adsorbent 20, dispersing material 70 or any other material permitting the release of aroma based upon a generated signal.

Disk 10 according to this embodiment of the invention, preferably has the dimensions of a conventional CD-ROM and is suitable for playing in a conventional CD player. According to an alternative embodiment of this invention, a specialized CD player capable of reading two sides of disk 10 simultaneously may be used in connection with disk 10 so as to read first side 61 and second side 63.

Experimental Procedure

Figure 5:
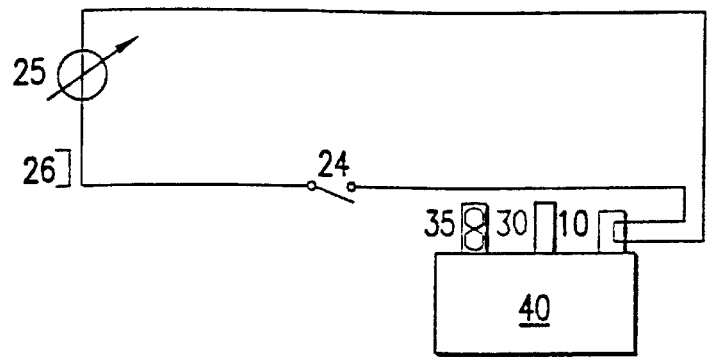
FIG. 5 is schematic view of the apparatus according to one preferred embodiment of this invention.

An experimental apparatus was developed to test different polymeric membranes for permeation of odor. A schematic of the experimental apparatus is shown in FIG. 5. In one preferred embodiment of the subject invention, controller 25 comprises a variable transformer (VARIAC) for distributing the appropriate currents to input 14 of disk drive 40.

In one preferred embodiment of this invention, disk 10 comprises six pairs of inputs electrically connected with six corresponding membrane modules 17 arranged in a row. Each membrane module 17 in this experimental embodiment comprises conductive element 18 surrounded with semi-porous membrane 22. For the purposes of this experiment, semi-porous membrane 22 is formed into a tube surrounding conductive element 18.

Several polymeric materials including Teflon, Tygon and silicon rubber were tested for use as semi-porous membrane 22. Silicon rubber was chosen for this experiment based upon its beneficial characteristics. The silicon rubber was formed into tubes, having an internal surface and an external surface, for use as semi-porous membrane 22 of membrane module 17. For this experiment, silicon rubber tubing approximately 2 inches in length were used as semi-porous membrane 22. Various thicknesses of semi-porous membrane 22 were investigated.

Appropriate aroma solutions, in this case various commercially available perfumes, were injected, each in a separate membrane module 17, between the annulus formed between conductive element 18 and semi-porous membrane 22. Aroma solution was drained from semi-porous membrane 22 after an appropriate soaking time, in this case approximately 48 hours. Alternatively, aroma solution may remain within semi-porous membrane 22. In another preferred embodiment, the external surface of semi-porous membrane 22 was soaked with aroma solution. In this experiment, each membrane module 17 was filled with 0.2 ml of perfume.

Each membrane module 22 was assembled using conductive element 18 made with 24 BNC Nickel-Chrome resistance wire. Conductive element 18 was fed through the center of semi-porous membrane 17 and each end of semi-porous membrane 22 was sealed using a fast-setting aluminum epoxy. For this experiment, a Teflon sleeve was applied between conductive element 18 and semi-porous membrane 17 to prevent direct contact of the hot conductive element 18 with the semi-porous membrane 17.

Membrane modules 22 containing semi-porous membranes 17 treated with the aroma solution were then connected to power source 26. For experimental purposes, a 110 Volt power source 22 was transformed into approximately 3–4 Volts prior to application to membrane module 17.

Fan 35 with a flow rate of about 32 cfm was used as exhaust 35 to disseminate the fragrance of the aroma solution. In one preferred embodiment of this invention, air flow from fan 35 was directed over an exposed upper surface of membrane modules 17. In another, alternate embodiment air flow was directed beneath the surface of membrane modules 17 through slots or compartment 52, shown in FIG. 6, constructed under each membrane module 17.

In yet another embodiment of this invention, shown in FIG. 6, membrane module 17 is moveable from a first position within upper compartment 50 to a second position in lower compartment 52. In this preferred embodiment of the invention, selected membrane module 17' is positioned in the path of air flow from fan 35 (not shown in FIG. 6).

A K-type thermocouple measured the surface temperature of each conductive element 18. The resulting electric signal was then recorded using a Strawberry Tree™ data acquisition and control system on a personal computer. The temperature of conductive element 18 was then controlled by the same system. The optimum temperature of conductive element 18, that is, the highest temperature possible without altering the properties of the aroma solution or damaging membrane module 17 was obtained by trial and error.

Experimental Results

Two air flow paths were tested, over the upper, exposed surface of membrane modules 17 and beneath the surface of membrane modules 17. Experimental results revealed that air flow over the upper surface of membrane module 17 results in better dispersal of the scent generated by membrane module 17. Directing the air beneath the surface of membrane modules 17 results in scents from differently scented membrane modules 17 intermingling. Membrane module 17' positioned in the path of air flow from fan 35 greatly reduced the mixing of scents from the various unselected membrane modules 17.

Tests also revealed that, to avoid mixing different scents among membrane modules 17, a delay of at least 15 seconds is necessary between the deactivation of one membrane module 17 and the activation of a different membrane module 17. However, such a delay was unnecessary in the embodiment of this invention wherein membrane module 17' is moveable to a second position.

Test results revealed that the thickness of semi-porous membrane 22 was proportional to the time lag for detection of the scent of membrane module 17. Experimental results also revealed that soaking only the inner surface of the semi-porous membrane 22 results in better dissemination of the scent from membrane module 17. Membrane module 17 could be reused many times before requiring replacement and/or reapplication of aroma solution.

Because each perfume has different characteristics, the required temperature of conductive element 18 was different for each brand of perfume. This suggests that the selection of the temperature should be done automatically when the type of aroma solution, such as a brand of perfume, is specified.

While in the foregoing specification this invention has been described in relation to certain preferred embodiments thereof, and many details have been set forth for purposes of illustration, it will be apparent to those skilled in the art that the apparatus is susceptible to additional embodiments and that certain of the details described herein can be varied considerably without departing from the basic principles of the invention.

We claim:

1. An apparatus for generating odor, the apparatus comprising:
   a substrate;
   a dispersing material comprising a compound having reversible properties, the dispersing material retaining at least one releasable aroma positioned on the substrate; and
   a device for providing a stimulus to the dispersing material upon demand as a function of a signal, wherein at least one physical property of the dispersing material is reversibly altered as a result of the stimulus so that the dispersing material responsively reacts to the stimulus resulting in a controlled release of aroma and subsequently returns to an unaltered state resulting in containment of the aroma.

2. An apparatus for generating odor, the apparatus comprising:
   a substrate;
   a smart material having a plurality of openable pores retaining at least one releasable aroma positioned on the substrate, the smart material comprising a polymer having reversible physical properties; and
   a device for providing a stimulus to the smart material upon demand as a function of a signal, wherein at least one physical property of the smart material is reversible altered as a result of the stimulus so that the dispersing material responsively reacts to the stimulus resulting in a controlled release of aroma and subsequently returns to an unaltered state resulting in containment of the aroma.

3. The apparatus of claim 2 wherein the smart material is selected from the group of PNIPAAM, allyl-substituted polyethylene glycol cross-linked by a silicon-based compound, allyl-substituted polyethylene glycol cross-linked by tetrakis (dimethylsiloxy) silane, a silicone formulation and combinations thereof.

4. The apparatus of claim 2 wherein the device provides a chemical stimulus.

5. The apparatus of claim 2 wherein the device provides an optical stimulus.

6. The apparatus of claim 2 wherein the device provides a thermal stimulus.

7. The apparatus of claim 6 wherein the device is a laser.

8. The apparatus of claim 2 wherein the device provides a magnetic stimulus.

9. The apparatus of claim 2 wherein the device provides an electromagnetic stimulus.

10. The apparatus of claim 2 further comprising a reflective layer positioned on the material.

11. The apparatus of claim 1 wherein the dispersing material comprises one of stimuli-response polymers and stimuli-response gels, that burst in response to the stimulus.

12. The apparatus of claim 1 wherein the dispersing material comprises tiny encapsulated globules of an immiscible combination of polymer solution and aroma compound.

13. The apparatus of claim 1 wherein the dispersing material is grafted onto a polymer support which is positioned on the substrate.

14. The apparatus of claim 13 wherein the polymer support is selected from one of the group of: polyvinyliddene fluoride, silicone compounds, polysolofone, cellulose fiber and polystyrene.

15. The apparatus of claim 14 wherein the polymer support comprises at least two layers of high and low porosity and at least two surface areas.

16. The apparatus of claim 1 wherein the dispersing material comprises a polymer and the substrate comprises a porous metal having a high thermal expansion coefficient.

17. An apparatus for generating odor, the apparatus comprising:
    a substrate;
    a dispersing material retaining at least one releasable aroma positioned with respect to the substrate, the dispersing material comprising a polymeric smart material having reversible properties with a microscopic structure including a plurality of openable pores; and
    a device for providing a stimulus to the dispersing material upon demand as a function of a signal, wherein a size of each of the plurality of pores is reversibly altered as a result of the stimulus so that the plurality of pores responsively enlarge and contract resulting in a controlled release of aroma.

18. The apparatus of claim 17 further comprising a reflective layer positioned on the dispersing material.

19. The apparatus of claim 18 wherein the reflective layer comprises gold.

20. The apparatus of claim 17 wherein the device comprises a laser.

21. An apparatus for generating odor, the apparatus comprising:
    a substrate;
    a dispersing material retaining at least one releasable aroma positioned with respect to the substrate, the dispersing material comprising a polymer having reversible physical properties; and
    a device for providing heat to the dispersing material upon demand as a function of a signal, wherein a plurality of pores within the dispersing material are reversibly enlarged as a result of the heat resulting in a controlled release of aroma and wherein the plurality of pores within the dispersing material subsequently contract when heat is removed resulting in containment of aroma.

22. The apparatus of claim 21 wherein the dispersing material comprises one of PNIPAAM grafted on polyvinylidene fluoride and a silicone formulation.

23. The apparatus of claim 21 further comprising a reflective layer positioned on the dispersing material.

24. An apparatus for generating odor, the apparatus comprising:
    a substrate;
    a dispersing material retaining at least one releasable aroma positioned with respect to the substrate;
    a device for providing heat to the dispersing material upon demand as a function of a signal, wherein a plurality of pores within the dispersing material are reversibly enlarged as a result of the heat; and
    readable medium positioned with respect to the substrate, the readable medium containing at least one of audio and video.

25. The apparatus of claim 21 wherein the device comprises a laser.

26. The apparatus of claim 25 wherein the dispersing material comprises a polymer material insensitive to a wavelength of emitted light from the laser.

27. A disk for generating odor comprising:

a substrate;

a first readable medium containing at least one of audio and video positioned on a first side of the substrate; and a second readable medium containing a releasable odor on a second side of the substrate opposite the first side.

28. The disk of claim 27 further comprising a reflective layer positioned on the second readable medium.

29. The disk of claim 27 wherein the second readable medium comprises a smart material having a plurality of openable pores.

30. The disk of claim 27 wherein the substrate comprises a conductive metal.

31. The disk of claim 27 wherein the second readable medium comprises a plurality of encapsulated spheres.

32. The disk of claim 27 having the dimensions of a CD-ROM.

33. A disk for generating odor comprising:

a substrate; and a dispersing material positioned on the substrate, the dispersing material having a plurality of pores that reversibly expand and contract in response to a stimulus, the dispersing material comprising a smart material selected from the group of PNIPAAM, allyl-substituted polyethylene glycol cross-linked by a silicon-based compound and allyl-substituted polyethylene glycol cross-linked by tetrakis (dimethylsiloxy) silane.

34. An apparatus for generating odor, the apparatus comprising:

a substrate;

a dispersing material retaining at least one releasable aroma positioned on the substrate; and a device for providing a stimulus to the dispersing material upon demand as a function of a signal, wherein at least one physical property of the dispersing material is reversibly altered as a result of the stimulus so that the dispersing material responsively reacts to the stimulus resulting in a controlled release of aroma and subsequently returns to an unaltered state resulting in containment of the aroma, the dispersing material comprising a smart material selected from the group of PNIPAAM, allyl-substituted polyethylene glycol cross-linked by a silicon-based compound and allyl-substituted polyethylene glycol cross-linked by tetrakis (dimethylsiloxy) silane.

35. An apparatus for generating odor, the apparatus comprising:

a substrate;

a smart material having a plurality of openable pores retaining at least one releasable aroma positioned on the substrate, wherein the smart material is rejected from the group of PNIPAAM, allyl-substituted polyethylene glycol cross-linked by a silicon-based compound, allyl-substituted polyethylent glytol cross-linked by tetrakis (dimethylsiloxy) silane, a silicone formulation and combinations thereof; and a device for providing a stimulus to the smart material upon demand as a function of a signal, wherein at least one physical property of the smart material is altered as a result of the stimulus.

36. The apparatus of claim 35 wherein the device provides one of a chemical stimulus, an optical stimulus, a magnetic stimulus, an electro-magnetic stimulus and a thermal stimulus.

37. The apparatus of claim 35 wherein the device is a laser.

38. An apparatus for generating odor, the apparatus comprising:

a substrate;

a dispersing material retaining at least one releasable aroma positioned with respect to the substrate, the dispersing material comprising a smart material having a microscopic structure including a plurality of openable pores and is selected from the group of PNIPAAM, allyl-substituted polyethylene glycol cross-linked by a silicon-based compound, allyl-substituted polyethylene glycol cross-linked by tetrakis (dimethylsiloxy) silane, a silicone formulation and combinations thereof; and a device for providing a stimulus to the dispersing material upon demand as a function of a signal, wherein a size of each of the plurality of pores is reversibly altered as a result of the stimulus so that the plurality of pores responsively enlarge and contract resulting in a controlled release of aroma.

39. An apparatus for generating odor, the apparatus comprising:

a substrate;

a dispersing material retaining at least one releasable aroma positioned with respect to the substrate, wherein the dispersing material is a smart material is selected from the group of PNIPAAM, allyl-substituted polyethylene glycol cross-linked by a silicon-based compound, allyl-substituted polyethylene glycol cross-linked by tetrakis (dimethylsiloxy) silane, a silicone formulation and combinations thereof; and a device for providing heat to the dispersing material upon demand as a function of a signal, wherein a plurality of pores within the dispersing material are reversibly enlarged as a result of the heat resulting in a controlled release of aroma and wherein the plurality of pores within the dispersing material subsequently contract when heat is removed resulting in containment of aroma.

* * * * *